United States Patent [19]

Knoll et al.

[11] Patent Number: 4,921,960

[45] Date of Patent: * May 1, 1990

[54] QUINOLINE THIOETHERS

[75] Inventors: József Knoll; Katálin Budai née Simonyi; Edit Berényi née Poldermann; Ildikó Miklya; Márton Fekete; Gabriella Zsilla; Berta Knoll; Attila Mándi; Lujza Petöcz; István Gyertyán; István Gacsályi, all of Budapest, Hungary

[73] Assignee: BASF Aktiengesellschaft, Ludwigshafen, Fed. Rep. of Germany

[*] Notice: The portion of the term of this patent subsequent to May 1, 2007 has been disclaimed.

[21] Appl. No.: 184,796

[22] Filed: Apr. 22, 1988

[30] Foreign Application Priority Data

Apr. 24, 1987 [HU] Hungary ................ 1778/87

[51] Int. Cl.⁵ .................. C07D 215/36; A61K 31/47
[52] U.S. Cl. ...................... 546/153; 514/312
[58] Field of Search ................ 514/312; 546/153

[56] References Cited

U.S. PATENT DOCUMENTS 4,788,204 11/1988 Benavides et al. ............. 514/312

Primary Examiner—William R. Dixon, Jr.
Assistant Examiner—Miriam Sohn
Attorney, Agent, or Firm—Keil & Weinkauf

[57] ABSTRACT

The new compounds of the general Formula I

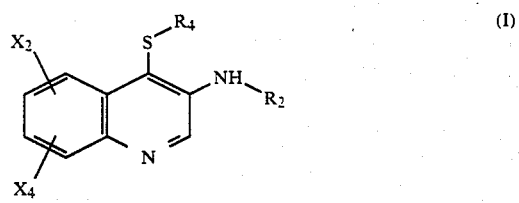

(wherein
$R_1$ stands for $C_{1-5}$ alkyl, $C_{2-5}$ alkenyl, $C_{2-5}$ alkinyl, $C_{3-7}$ cycloalkyl or optionally substituted phenyl-($C_{1-4}$ alkyl);
$R_2$ represents hydrogen or $C_{1-5}$ alkanoyl;
$X_1$ and $X_2$ can be identical or different and each stands for hydrogen, halogen, trifluoromethyl or $C_{1-4}$ alkoxy;

(with the proviso that if $R_1$ stands for ethyl, at least one of $R_2$, $X_1$ and $X_2$ is different from hydrogen) and pharmaceutically acceptable acid additions salts possess valuable anxiolytic properties devoid of sedative effect and can be used in therapy.

The compounds of the general Formula I can be prepared by methods known per se.

6 Claims, No Drawings

QUINOLINE THIOETHERS

This invention relates to new quinoline thioethers, a process for the preparation thereof and pharmaceutical compositions comprising the same.

3-Amino-4-ethylthio-quinoline has been described in prior art [Hiroyuki Sawanishi et al: Heterocycles, 22/7, 1501–1504 (1984)]. According to the citation the said compound is prepared by subjecting 3-azido-quinoline to photolysis or thermolysis in the presence of ethane thiol. The authors are, however, completely silent in disclosing any biological effect of 3-amino-4-ethylthio-quinoline.

According to an aspect of the present invention there are provided new quinoline thioethers of the general Formula I

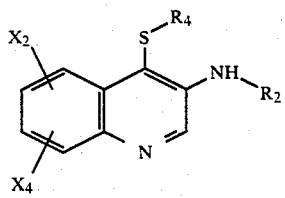

(I)

wherein
R$_1$ stands for C$_{1-5}$ alkyl, C$_{2-5}$ alkenyl, C$_{2-5}$ alkinyl, C$_{3-7}$ cycloalkyl or optionally substituted phenyl(C$_{1-4}$ alkyl);
R$_2$ represents hydrogen or C$_{1-5}$ alkanoyl;
X$_1$ and X$_2$ can be identical or different and each stands for hydrogen, halogen, trifluoromethyl or C$_{1-4}$ alkoxy;
with the proviso that if R$_1$ stands for ethyl, at least one of R$_2$, X$_1$ and X$_2$ is different from hydrogen) and pharmaceutically acceptable acid addition salts thereof.

The compounds of the general Formula I possess valuable pharmaceutical properties and are useful first of all as potent and selective anxiolytic agents. The particular advantage of the compounds of the general Formula 1 resides in their selective anxiolytic effect, i.e. the anxiolytic effect is practically devoid of sedative and anticonvulsive effects.

The term "C$_{1-5}$ alkyl" used throughout the specification relates to straight or branched chain alkyl groups (e.g. methyl, ethyl, n-propyl, isopropyl, n-butyl etc.). The term "C$_{2-5}$ alkenyl" designates straight or branched chain aliphatic hydrocarbon groups comprising at least one double bond (e.g. vinyl, allyl, 2-propenyl, methallyl etc.). The term "C$_{2-5}$ alkinyl" covers straight or branched chain aliphatic hydrocarbon groups comprising at least one triple bond (e.g. propargyl etc.). The term "C$_{3-7}$ cycloalkyl" relates to cycloalkyl groups as cyclopropyl, cyclobutyl, cyclopentyl, cyclohexyl etc. The term "phenyl-(C$_{1-4}$ alkyl)" relates to C$_{1-4}$ alkyl groups in which at least one hydrogen atom is replaced by a phenyl group (e.g. benzyl, β-phenylethyl) whereby the said group may optionally bear one or more identical or different substituent(s) (e.g. halogen, alkoxy, alkyl, nitro, amino, hydroxy, etc.).

The term "C$_{1-5}$ alkanoyl" relates to acid residues of the corresponding alkanoic acids (e.g. acetyl, propionyl, butyryl etc.).

The term "halogen" encompasses the fluorine, chlorine, bromine and iodine atoms.

The pharmaceutically acceptable acid addition salts of the compounds of the general formula I can be formed with pharmaceutically acceptable inorganic or strong organic acids (e.g. hydrochlorides, hydrobromides, hydroiodides, sulfates, perchlorates, ethanesulfonates etc.).

A particularly preferred representative of the compounds of the general Formula I is the 3-amino-4-ethylthio-7-chloro-quinoline and pharmaceutically acceptable acid addition salts thereof.

According to a further aspect of the present invention there is provided a process for the preparation of compounds of the general Formula I and pharmaceutically acceptable acid addition saltss thereof, which comprises (a) reacting a 3-amino-4-quinoline-thiol of the general Formula II

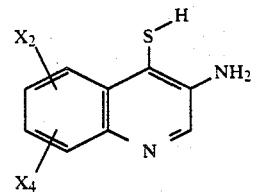

(II)

(wherein X$_1$ and X$_2$ are as stated above) or a salt thereof with a compound of the general Formula III

R$_1$—X    (III)

(wherein R$_1$ is as stated above and X stands for a leaving group); or (b) reacting a 3-nitro-4-haloquinoline of the general Formula IV

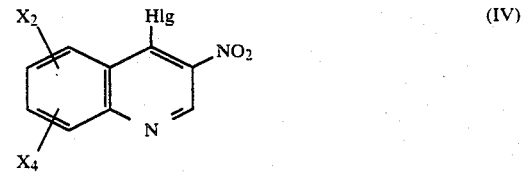

(IV)

(wherein Hlg stands for halogen and X$_1$ and X$_2$ are as stated above) with a mercapto compound of the general Formula V

R$_1$—SH    (V)

(wherein R$_1$ is as stated above) or a salt thereof and reducing the product thus obtained; or (c) reacting a 3-nitro-quinoline-4-thiol of the general Formula VI

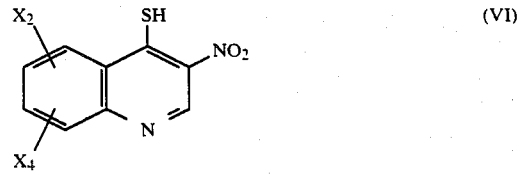

(VI)

(wherein X$_1$ and X$_2$ are as stated above) or a salt thereof with a compound of the general Formula III and reducing the product thus obtained;

and, if desired, acylating a compound of the general Formula I, wherein R$_2$ is hydrogen, into the corresponding compound of the general Formula I, wherein R$_2$ represents C$_{1-5}$ alkanoyl; and/or if desired, hydrolysing a compound of the general Formula I, wherein $R_2$ stands for $C_{1-5}$ alkanoyl, into the corresponding compound of the general Formula I, wherein $R_2$ represents hydrogen; and/or if desired, converting a compound of the general Formula I into a pharmaceutically acceptable acid addition salt thereof or setting free a compound of the general Formula I from an acid addition salt thereof.

According to process (a) a compound of the general Formula II is reacted with a compound of the general Formula III. Symbol X appearing in the compounds of the general Formula III represents preferably halogen (e.g. chlorine, bromine or iodine) or alkylsulfonyloxy (e.g. methylsulfonyloxy) or arylsulfonyloxy (e.g. phenylsulfonyloxy, p-bromophenylsulfonyloxy or p-tolylsulfonyloxy) as leaving group.

The alkylating agent of the general Formula III can be preferably used in an excess. The reaction may be carried out at a temperature between 20° C. and 160° C., preferably at the boiling point. The reaction may be accomplished in a polar solvent, particularly in aqueous medium. The compound of the general Formula I thus obtained can be isolated from the reaction mixture by known methods (e.g. cooling and filtration, or extracting).

According to process (b) a 4-halo-3-nitro-quinoline of the general Formula IV is reacted with a thiol of the general Formula V or a salt thereof whereupon the product thus obtained is reduced. The reaction of the compounds of the general Formulae IV and V can be carried out at a temperature between 20° C. and 160° C. The thiol of the general Formula V can also be used in the form of a salt (e.g. as alkali salt).

The reaction may be accomplished in a polar solvent. As reaction medium preferably an alkanol (e.g. methanol or ethanol), dimethyl sulfoxide or dimethyl formamide may be used. The product formed can be reduced to the desired amino compound of the general Formula I by methods known per se. It is preferred to use sodium sulfide as reducing agent and to work in an aqueous-alcoholic medium.

According to process (c) a 3-nitro-4-quinoline-thiol of the general Formula VI or a salt thereof is reacted with an alkylating agent of the general Formula III and the product thus obtained is reduced. The reaction of the compounds of the general Formulae VI and III can be accomplished at 20°-160° C., preferably under heating. The product thus obtained can be reduced to the desired amino compound by methods known per se. The nitro group is reduced to amino group preferably with the aid of sodium sulfide, as described in connection with process (b).

A compound of the general Formula I, wherein $R_2$ stands for hydrogen, can be acylated, if desired, into the corresponding compound of the general Formula I, wherein $R_2$ is $C_{1-5}$ alkanoyl. Acylation may be carried out in a manner known per se by using the corresponding alkanoic acid or a reactive derivative thereof. As reactive reaction acid derivative preferably an acid halide, acid anhydride or ester may be used. One may proceed preferably by acylating a compound of the general Formula I, wherein $R_2$ stands for hydrogen, with the corresponding acid anhydride. The said acid anhydride may also be used in an excess whereby it acts as reaction medium as well. The acylation may, however, also be accomplished in an inert organic solvent (e.g. pyridine) as medium. If acylation is carried out with the aid of an acid halide, it is preferred to work in the presence of an acid binding agent. For this purpose organic or inorganic bases (e.g. alkali carbonates, alkali hydrogen carbonates, triethyl amine etc.) can be used. Acylation may also be accomplished by using the corresponding free alkanoic acid, wherein it is preferred to work in the presence of a dehydrating agent (e.g. dicyclohexyl carbodiimide). Acylation may be advantageously carried out at 0°-40° C.

A compound of the general Formula I, wherein $R_2$ stands for alkanoyl, may be hydrolysed, if desired, into the corresponding compound of the general Formula I wherein $R_2$ is hydrogen. Hydrolysis can be accomplished by methods known per se, in acidic (e.g. hydrochloric acid) or alkaline (e.g. sodium hydroxide) medium.

A compound of the general Formula I can be converted into a pharmaceutically acceptable acid addition salt. Salt formation may be carried out in a manner known per se by reacting a base of the general Formula I with an equimolar amount of the corresponding acid in an inert solvent.

The starting materials of the general Formulae II and IV are partly known [Bachman et al: J. Am. Chem. Soc. 69, 365-371 (1947)] or can be prepared in a manner analogous to known compounds. The compounds of the general Formulae III and V are commercially available.

The pharmacological spectrum of 3-amino-4-ethylthio-7-chloro-quinoline-hydrochloride (referred to further as "compound A") is demonstrated by the following tests. The said compound A is a typical representative of the compounds of the general Formula I.

(1) ACUTE TOXICITY

Acute toxicity was assessed on CFY rats (100-160 g). Groups of 10 rats were used. Compound A was administered orally (in volume of 10 ml/kg). The animals starved for 16 h before the experiment. Each dose was administered to a group of animals equally subdivided into males and females. Deaths occurring within 48 h were considered. $LD_{50}$ values were calculated on the basis of the graphical method of Litchfield and Wilcoxon.

Oral $LD_{50}=465$ mg/kg

(2) MEASUREMENT OF THE ANTI-ANXIETY VERSUS SEDATIVE EFFECT OF COMPOUND A

The essential strategy for measuring the anti-anxiety effecct of a drug is to check its activity in a conflict situation. We elicit a rewarded response, then suppress that response by punishing it when it occurs and the anti-anxiety effect is measured by the drug-induced increase in punished responding, whereas the sedative effect is measured by the drug-induced decrease of unpunished responding.

A rat, deprived of food for 96 hours and supplied with water ad libitum, drinks about 7 ml water during the 4th day of food deprivation, but needs 35 ml water daily when supplied with dry food [for review see Knoll, J. J., Neural Transm. 59, 163-194 (1984)]. This means that when we circuit the drinking tube and the grid floor of the cage and the rat is regularly shocked by trying to drink, the very hungry animal, which cannot eat without drinking, is maximally forced to overcome the hindrance. This is a sensitive test to check the anti-anxiety effect of a compound.

Male CFY rats, weighing 230-250 g, fed with standard food pellets and supplied with tap water ad libitum, were kept under controlled standard environmental conditions (room temperature between 22°-24° C.) in groups of ten for two weeks until used in the experiment. The rats kept in single cages during starvation were deprived of food for 96 hours and supplied with tap water ad libitum before the experiment.

Only those animals which did not lose more than 80 g body weight during the starvation period were selected for the experiment. In our test, based on calculations from the changes in 550 male rats deprived of food for 96 hours, the average loss of body weight was found to be 66 g.

Another aspect of the selection of the animals for the experiment was their visible physical fitness and normal activity after starvation. Less than 10 percent of the rats were excluded from the experiment because of insufficient physical fitness.

A clear Plexiglass box (39×27×12 cm) with a stainless-steel grid floor supplied with a tray for the food pellets and with a drinking tube was used for the experiment. The grid floor, the drinking tube and an electric stimulator (Grass S48) were connected and electric shocks in this circuit were delivered for 10 s duration with 20 s intervals. The parameters of the current (100 V; 25 ohm; 7.5 ms; 5 Hz) were empirically selected using those electric shocks which inhibited the water consumption of the very hungry rats to one third of the control (unpunished) level.

The rats spend one hour in the apparatus after 96 hours of food deprivation. The very hungry rats eat 5–6 g of food pellets during the first hour of the feeding period after the long starvation. The water consumption of the hungry rats during the first hour of the feeding period was measured in groups of rats without punishment and was found to be 6–7 ml. In the punished situation the consumption was reduced to less than 3 ml.

The drugs were administered parenterally in doses of 0.5 ml/100 g body weight. We refrained from the oral administration of the compounds because of the long term food deprivation.

The Student t-test was used for statistical analysis. The anxiolytic effect was established in punished animals and the sedative effect in unpunished rats.

The anti-anxiety versus sedative effect of chlordiazepoxide, as a reference substance, is shown in Table I. Chlordiazepoxide exerted in the subcutaneous dose of 0.1 mg/kg its characteristic anxiolytic effect, whereas the sedative dose range was 10 mg/kg.

As chlordiazepoxide acts by being the agonist on benzodiazepine receptors, the anxiolytic effect of this drug is antagonized by RO-15-1788 which is selective benzodiazepine receptor antagonist. This is shown in Table II.

Table III shows the antianxiety effect of compound A. This compound is about 20 times more potent than chlordiazepoxide in this test as an anti-anxiety agent. The anxiolytic activity of compound A was antagonized by RO-15-1788 as shown in Table IV.

Whereas the ratio between the sedative and anxiolytic dose (see Table I) was found to be 10 per 0.1=100 in the case of chlordiazepoxide, this ratio proved to be 2.5 per 0.005=500 in the case of compound A (see Table III).

(3) MEASUREMENT OF THE BINDING OF COMPOUND A TO BENZODIAZEPINE RECEPTORS

The in vitro binding of compound A in comparison to that of chlordiazepoxide was measured on rat brain membrane preparation. Male CFY rat cortex was homogenized in 0.32M sucrose using glass homogenizer with teflon pestle. Nucleus was spun down at 1000 g for 15 min. The supernatant was centrifuged at 40,000 g for 15 min. The pellet was homogenized in 5 mM TRIS-citrate buffer pH 7.1 by a Polytron P10 and it was lyzed for 15 min. at 0° C. After centrifugation at 40,000 g for 15 min. the pellet was taken up in 50 mM TRIS-citrate buffer pH 7.1 and kept overnight at −20° C. After thawing and centrifugation (40,000 g for 15 min.) the pellet was washed in 50 mM TRIS-citrate buffer pH 7.1 three times by centrifugation. The final pellet was taken up in the same buffer in 1:30 volume. Ligand: 2 nM $^3$H-Diazepam (sp. act. 86 Ci/mmol).

Incubation: 1 hr at 0°–4° C. in 50 mM TRIS-citrate buffer ph 7.1
Final volume: 0.25 ml
Final protein concentration: ca. 0.5 mg/ml.

The binding was stopped by dilution with cold buffer and rapid filtration on GF/B Whatman filter paper.

For the displacement we used six different concentrations of drugs, run with 3 parallels. Experiments were repeated two times. Compound A was dissolved in cc. acetic acid and distilled water then the $10^{-3}$M solution was further diluted with incubation buffer. Blank solution was prepared in the same way without containing the drug. Chlordiazepoxide was dissolved in the incubation buffer.

Chlordiazepoxide and compound A displaced $^3$H-Diazepam from its receptor in a concentration dependent manner. The IC$_{50}$ value for both drugs is in the same range of concentration. As the blank did not displace the isotope labelled diazepam at concentrations less than $10^{-4}$M, the influence of acetic acid in the effect of compound A could be excluded.

(4) MEASUREMENT OF THE EFFECT OF COMPOUND A AGAINST ELECTROGENIC AND DRUG-INDUCED CONVULSIONS

Compound A up to the oral dose of 200 mg/kg proved to be ineffective in protecting against either pentametazol, strychnine and picrotoxin induced convulsions and was only slightly effective against electroshock-induced convulsions in rats.

The subcutaneous injection of 120 mg/kg of pentametazol induced tonic extensions in both the fore and hind limbs of the rats and killed 100% of the animals. The administration of 10 mg/kg of diazepam or phenobarbital Na prior to 120 mg/kg pentametazol mitigated the convulsions, was life protecting, none of the pretreated animals died. Even the pretreatment of the rats with 200 mg/kg of compound A did not change the severity of the pentametazol convulsions, none of the pretreated animals survived.

Compound A (200 mg/kg) had no influence on the anticonvulsant effect of diazepam (10 mg/kg).

Strychnine (2.5 mg/kg, s.c.) induced lethal convulsions were incompletely antagonized by 50 mg/kg of phenobarbital Na (40% died) and 10 mg/kg of diazepam (80% died) and was not influenced at all by compound A up to the 200 mg/kg dose level.

Picrotoxin (10 mg/kg, s.c.) induced lethal convulsions were slightly infuenced by 50 mg/kg of phenobarbital Na (80% died) and remained unchanged in rats pretreated with either diazepam or compound A.

Electroshock-induced lethal convulsions were slightly influenced by 200 mg/kg of compound A (70% of the animals died). Rats pretreated with phenobarbital Na (30–50 mg/kg) were completely protected against electrogenic convulsions and diazepam saved the life of 80% of the rats.

In conclusion compound A is in the animal test a potent and selective anxiolytic agent. Its anti-anxiety effect seems to be related to benzodiazepine receptors, but in striking contrast to benzodiazepines, in clinical use compound A is practically devoid of sedative and anticonvulsant activities.

TABLE I

The effect of chlordiazepoxide on unpunished and punished behavior in the described "conflict" test

| Series of experiment | Dose mg/kg | Water consumption (ml) without punishment | Water consumption (ml) punished situation |
|---|---|---|---|
| 1 | none | 5.8 ± 0.32 (10) | 2.8 ± 0.44 (10) |
| 2 | 0.05 | 5.1 ± 0.56 (10) | 3.5 ± 0.47 (15) |
| 3 | 0.1 | 5.8 ± 0.42 (10) | 4.1 ± 0.31$^x$ (30) |
| 4 | 0.25 | 6.2 ± 0.37 (10) | 3.5 ± 0.62 (10) |
| 5 | 0.5 | 7.4 ± 0.77 (10) | 3.1 ± 0.54 (10) |
| 6 | 1 | 5.4 ± 0.68 (10) | 2.7 ± 0.58 (10) |
| 7 | 2.5 | 5.2 ± 0.72 (10) | 4.1 ± 0.39$^x$ (10) |
| 8 | 5 | 5.4 ± 0.62 (15) | 2.5 ± 0.31 (10) |
| 9 | 10 | 1.8 ± 0.30$^{xx}$ (10) | 1.6 ± 0.26$^x$ (10) |

Chlordiazepoxide was administered subcutaneously 30 minute prior to experiment. Number of animals in parentheses. Significance:
$^x p < 0.05$
$^{xx} p < 0.001$

TABLE II

The antagonism of the anti-anxiety effect of chlordiazepoxide by RO 15-1788 in the described "conflict" test

| Series of experiment | Dose of chlordiazepoxide mg/kg | RO 15-1788 mg/kg | Water consumption (ml) in punished situation | Significance |
|---|---|---|---|---|
| 1 | none | none | 2.8 ± 0.44 (10) | |
| 2 | 0.1 | none | 4.1 ± 0.31 (30) | 1 : 2 < 0.05 |
| 3 | 0.1 | 5 | 4.1 ± 0.59 (10) | 2 : 3 n. s. |
| 4 | 0.1 | 10 | 3.9 ± 0.43 (15) | 2 : 4 n. s. |
| 5 | 0.1 | 20 | 2.8 ± 0.49 (15) | 2 : 5 p < 0.05 |

Chlordiazepoxide was administered subcutaneously and RO 15-1788 was given intraperitoneally 30 minutes prior to experiments. Number of animals in parenthesis.

TABLE III

The effect of compound A on unpunished and punished behaviour in the described "conflict" test

| Series of experiment | Dose | Water consumption (ml) without punishment | Water consumption (ml) punished situation |
|---|---|---|---|
| 1 | none | 7.2 ± 0.84 (10) | 2.7 ± 0.35 (21) |
| 2 | 2.5 γ/kg | 6.3 ± 0.46 (10) | 2.2 ± 0.32 (20) |
| 3 | 5 γ/kg | 6.4 ± 0.33 (30) | 3.8 ± 0.19$^x$ (80) |
| 4 | 25 γ/kg | 7.9 ± 0.58 (10) | 3.7 ± 0.44 (15) |
| 5 | 0.25 mg/kg | 7.7 ± 0.45 (10) | 3.0 ± 0.27 (30) |
| 6 | 2.5 mg/kg | 4.9 ± 0.91$^x$ (15) | 1.9 ± 0.35 (10) |

Compound A was administered subcutaneously 30 minutes prior to experiment. Number of animals in parentheses. Significance: $^x p < 0.001$

TABLE IV

The antagonism of the anti-anxiety effect of compound A by RO 15-1788 in the described "conflict" test

| Series of experiment | Dose of Compound A /μg/kg | RO 15-1788 mg/kg | Water consumption (ml) in punished situation | Significance |
|---|---|---|---|---|
| 1 | none | none | 2.7 ± 0.35 (21) | |
| 2 | 5 | none | 4.2 ± 0.37 (19) | 1 : 2 p < 0.01 |
| 3 | 5 | 10 | 3.1 ± 0.69 (8) | 2 : 3 p > 0.05 |
| 4 | 5 | 20 | 2.4 ± 0.39 (9) | 2 : 4 p < 0.01 |

Compound A was administered subcutaneously and RO 15-1788 was given intraperitoneally 30 minutes prior to experiments. Number of animals in parenthesis.

According to a further feature of the present invention there are provided pharmaceutical compositions comprising at least one compound of the general Formula I or a pharmaceutically acceptable acid addition salt thereof as carrier in admixture with suitable inert solid or liquid pharmaceutical carriers.

The active ingredient may be finished in forms suitable for oral (e.g. tablet, pill, coated pill, dragée, hard or soft gelatine capsule, solution, emulsion, suspension), parenteral (e.g. injectable solution) or rectal (e.g. suppository) application.

The pharmaceutical compositions of the present invention can be prepared by methods of pharmaceutical industry known per se. The compound of the general Formula I or a pharmaceutically acceptable acid addition salt thereof is admixed with inert, solid or liquid, organic or inorganic pharmaceutical carriers and/or excipients and the mixture is brought into a galenic form.

Tablets, pills, coated pills, dragées and hard gelatine capsules may comprise as carrier e.g. lactose, maize starch, potato starch, talc, magnesium carbonate, magnesium stearate, calcium carbonate, stearic acid or salts thereof etc. The soft gelatine capsules may comprise as carrier e.g. vegetable oils, fats, waxes or polyols of suitable consistence etc. In the preparation of solutions or syrups e.g. water, polyols, polyethylene glycol, saccharose or glucose may be used as carrier. The injectable solutions may comprise e.g. water, alcohols, polyols, glycerol or vegetable oils as carrier.

In the preparation of suppositories e.g. oils, waxes, fats and polyols of suitable consistence may be used as carrier.

The pharmaceutical compositions of the present invention may also comprise conventional auxiliary agents generally used in pharmaceutical industry (e.g. wetting, dispersing, conserving, emulsifying agents, dyes, sweetening agents, aroma materials, salts for modifying the osmotic pressure, buffers etc.). The pharmaceutical compositions of the present invention can comprise further therapeutically valuable materials, too.

It is preferred to use the compounds of the general Formula I in forms suitable for oral application, particularly as tablets or capsules. It is particularly preferred to use tablets or capsules having an active ingredient content of from about 2.5 mg to about 50 mg as dosage forms.

The daily dose of the compounds of the general Formula I may vary between wide ranges and depends on various factors (e.g. efficiency of the active ingredient, condition and age of the patient, severeness of the disease etc.). The daily oral dose may be approximately about 1–300 mg while the daily parenteral dose generally amounts to about 0.5–150 mg. It is to be emphasized that the above dose intervals are but of an informative character and the actual dose may be lower or higher as well and is always determined by the physician.

According to a further aspect of the present invention there is provided the use of a compounds of the general Formula I or a pharmaceutically acceptable acid addition salt thereof for the preparation of pharmaceutical compositions having anxiolytic effect.

According to a still further aspect of the present invention there is provided a method of anxiolytic treatment which comprises administering to the patient an effective dose of a compound of general Formula I or a pharmaceutically acceptable acid addition salt thereof.

Further details of the present invention are to be found in the following Examples without limiting the scope of protection to the said Examples.

EXAMPLE 1

17.62 g (0.1 mole) of 3-amino-4-quinoline-thiol are dissolved in 50 ml of a 2 molar sodium hydroxide solution, whereupon at a temperature below 40° C. 21.29 g (0.15 mole) of methyl iodide are added. The reaction mixture is stirred at 40° C. for an hour, extracted with chloroform, clarified with activated charcoal and evaporated. Thus 18.6 g of 3-amino-4-methylthio-quinoline are obtained, yield 94.6%, m.p.: 96°–98° C. (from methanol).

19 g (0.1 mole) of the above base are dissolved in 150 ml of ethyl acetate, whereupon ethanol containing hydrogen chloride is added. Thus 21 g of 3-amino-4-methylthio-quinoline-hydrochloride are obtained, yield 95%, m.p.: 228°–229° C. (decomposition).

EXAMPLES 2–11

In a manner analogous to Example 1 the following compounds enumerated in Table V are prepared:

TABLE V

| Example No. | Compound | Yield % | M.p. °C. |
|---|---|---|---|
| 2 | 3-amino-4-(n-propylthio)-quinoline.HCl | 80 | 168–170 |
| 3 | 3-amino-4-benzylthio-quinoline.HCl | 85 | 214–215 |
| 4 | 3-amino-7-chloro-4-methylthio-quinoline.HCl | 84 | 235–237 |
| 5 | 3-amino-4-ethylthio-7-chloro-quinoline.HCl | 80 | 214–216 dec. |
| 6 | 3-amino-7-chloro-4-isopropylthio-quinoline.HCl | 78 | 232–233 dec. |
| 7 | 3-amino-7-chloro-4-(n-propylthio)-quinoline.HCl | 86 | 209–210 dec. |
| 8 | 3-amino-4-allylthio-7-chloro-quinoline.HCl | 82 | 210–212 |
| 9 | 3-amino-7-chloro-4-propargylthio-quinoline.HCl | 84 | 222–223 |
| 10 | 3-amino-4-benzylthio-7-chloro-quinoline.HCl | 80 | 228–230 |
| 11 | 3-amino-7-chloro-4-(4-chlorobenzylthio)-quinoline.HCl | 85 | 215 dec. |

EXAMPLE 12

21.06 g (0.1 mole) of 3-amino-7-chloro-4-quinoline-thiol are dissolved in 100 ml of a 2 molar sodium hydroxide solution, whereupon 23.30 g (0.125 mole) of ethyl benzene sulfonate are added. The reaction mixture is heated to boiling for 2 hours and the product thus formed is extracted with chloroform. The chloroform solution is clarified with activated charcoal, dried and acidified with alcohol containing hydrogen chloride. Thus 24.0 g of 3-amino-4-ethylthio-7-chloro-quinoline-hydrochloride are obtained. After crystallization from methanol the product melts at 212°–216° C. under decomposition. Yield 85%. The product thus obtained is identical with the compound prepared according to Example 5.

EXAMPLE 13

22.67 g (0.1 mole) of 3-amino-4-methylthio-quinoline-hydrochloride [or 19.02 g (0.1 mole) of the corresponding base] are dissolved in 125 ml of pyridine, whereupon 10.7 g (0.105 mole) of acetic anhydride are added at 10°–15° C. When the yellow colour of the solution has disappeared, the reaction mixture is poured into 1000 ml of water. The precipitated white crystals are filtered. Thus 20.9 g of 3-acetylamino-4-methylthio-quinoline are obtained, yield 90%, m.p.: 137°–138° C. (after crystallization from ethyl acetate).

EXAMPLES 14–19

In a manner analogous to the process disclosed in Example 13 the following compounds enumerated in Table VI are prepared:

TABLE VI

| Example No. | Compound | Yield % | M.p. °C. |
|---|---|---|---|
| 14 | 3-acetylamino-7-chloro-4-methylthio-quinoline | 88 | 168–170 |
| 15 | 3-acetylamino-4-ethylthio-quinoline | 91 | 141–143 |
| 16 | 3-acetylamino-4-ethylthio-7-chloro-quinoline | 90 | 163–165 |
| 17 | 3-acetylamino-4-(n-propylthio)-quinoline | 92 | 103–105 |
| 18 | 3-acetylamino-7-chloro-4-isopropylthio-quinoline | 89 | 144–147 |
| 19 | 3-acetylamino-7-chloro-4-propargyl- | | |

TABLE VI-continued

| Example No. | Compound | Yield % | M.p. °C. |
|---|---|---|---|
| | thio-quinoline | 92 | 175–176 |

EXAMPLE 20

21.06 g (0.1 mole) of 3-amino-7-chloro-4-quinoline-thiol are dissolved in 100 ml of a 2 molar sodium hydroxide solution, whereupon 19.27 g (0.125 mole) of diethyl sulfate are added. The reaction mixture is heated to boiling for 2 hours, cooled to room temperature and extracted with dichloro ethane. The dichloro ethane solution is dried, clarified and evaporated. Thus 20.2 g of 3-amino-4-ethylthio-7-chloro-quinoline are obtained, yield 85%, m.p.: 105°–106° C. (after crystallization from methanol).

11.9 g (0.05 mole) of the above base are dissolved in 150 ml of ethyl acetate, whereupon ethanol containing hydrogen chloride is added. The precipitated crystals are filtered. Thus 13.0 g of 3-amino-4-ethylthio-7-chloro-quinoline-hydrochloride are obtained, yield 95%, m.p.: 212°–216° C. The product is identical with the compound prepared according to Example 5.

EXAMPLE 21

In a manner analogous to the process disclosed in Example 20 3-amino-7-chloro-4-methylthio-quinoline-hydrochloride is obtained, yield 80%, m.p.: 235°–237° C.

What we claim is:

1. A compound of the formula I

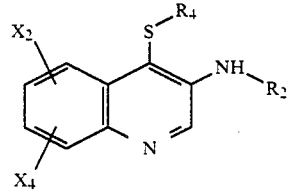

wherein $R_1$ stands for $C_{1-5}$ alkyl, $C_{2-5}$ alkenyl, $C_{2-5}$ alkinyl, $C_{3-7}$ cycloalkyl or unsubstituted or halo, alkoxy, alkyl, nitro, amino or hydroxy substituted phenyl or $C_1$–$C_4$-alkylphenyl;

$R_2$ represents hydrogen or $C_{1-5}$ alkanoyl;

$X_1$ and $X_2$ can be identical or different and each stands for hydrogen, halogen, trifluoromethyl or $C_{1-4}$ alkoxy;

with the proviso that if $R_1$ stands for ethyl, at least one of $R_2$, $X_1$ and $X_2$ is different from hydrogen, and pharmaceutically acceptable acid addition salts thereof.

2. The compound of claim 1 which is 3-Amino-4-ethylthio-7-chloro-quinoline and pharmaceutically acceptable acid addition salts thereof.

3. A pharmaceutical composition having anti-anxiety properties containing as an active ingredient at least one compound of the formula I as defined in claim 1 or a pharmaceutically acceptable acid addition salt thereof in admixture with an inert pharmaceutical carrier.

4. A method of administering an anxiolytic treatment to a patient in need thereof which comprises: administering to the patient an effective dose of a compound of the formula I as defined in claim 1 or a pharmaceutically acceptable acid addition salt thereof.

5. A pharmaceutical composition as defined in claim 3, whrein the active ingredient is 3-amino-4-ethylthio-7-chloroquinoline or a pharmaceutically acceptable acid addition salt thereof.

6. A method as defined in claim 4, wherein the compound is 3-amino-4-ethylthio-7-chloro-quinoline or a pharmaceutically acceptable acid addition salt thereof.

* * * * *

UNITED STATES PATENT AND TRADEMARK OFFICE
CERTIFICATE OF CORRECTION

PATENT NO. : 4,921,960

DATED : May 1, 1990

INVENTOR(S) : Jozsef KNOLL et al.

It is certified that error appears in the above-identified patent and that said Letters Patent is hereby corrected as shown below:

Title page:

Named assignee "BASF Aktiengesellschaft, Ludwigshafen, Fed. Rep. of Germany" should read--EGIS Gyogyszergyar, Budapest, Hungary--

Signed and Sealed this

Twenty-fifth Day of June, 1991

Attest:

HARRY F. MANBECK, JR.

Attesting Officer

Commissioner of Patents and Trademarks